United States Patent
Berberich et al.

(10) Patent No.: US 8,128,651 B2
(45) Date of Patent: Mar. 6, 2012

(54) MEDICAL INSTRUMENT

(75) Inventors: Sascha Berberich, Tuttlingen (DE); Egon Deufel, Friedingen (DE)

(73) Assignee: Karl Storz GmbH & Co. KG (DE)

( * ) Notice: Subject to any disclaimer, the term of this patent is extended or adjusted under 35 U.S.C. 154(b) by 1460 days.

(21) Appl. No.: 11/430,583

(22) Filed: May 9, 2006

(65) Prior Publication Data
US 2006/0282117 A1   Dec. 14, 2006

(30) Foreign Application Priority Data
May 9, 2005   (DE) .......................... 10 2005 021 234

(51) Int. Cl.
*A61B 17/00*   (2006.01)
(52) U.S. Cl. ........................................ 606/207
(58) Field of Classification Search .................. 606/205, 606/206, 207, 208; 81/346
See application file for complete search history.

(56) References Cited

U.S. PATENT DOCUMENTS

| | | | | |
|---|---|---|---|---|
| 2,894,324 A | * | 7/1959 | Hardin | 30/240 |
| 3,687,373 A | * | 8/1972 | Cornelius | 239/738 |
| 4,258,716 A | | 3/1981 | Sutherland | 128/318 |
| 4,499,899 A | * | 2/1985 | Lyons, III | 606/170 |
| 4,590,936 A | * | 5/1986 | Straub et al. | 606/174 |
| 5,052,660 A | * | 10/1991 | Bergman | 254/134.3 FT |
| 5,707,379 A | * | 1/1998 | Fleenor et al. | 606/145 |
| 2005/0090811 A1 | * | 4/2005 | Doyle et al. | 606/1 |

FOREIGN PATENT DOCUMENTS

| | | |
|---|---|---|
| DE | 83 02 716 | 5/1983 |
| DE | 695 32 486 T2 | 12/2004 |
| DE | 103 27 655 A1 | 1/2005 |
| EP | 0 003 668 B1 | 11/1981 |
| EP | 0 677 275 | 10/1995 |
| WO | WO 91/02493 | 3/1991 |

OTHER PUBLICATIONS

European Search Report, Aug. 25, 2006, 6 pages.

* cited by examiner

*Primary Examiner* — Gary Jackson
*Assistant Examiner* — Jonathan Hollm
(74) *Attorney, Agent, or Firm* — St. Onge Steward Johnston & Reens LLC

(57) ABSTRACT

The invention relates to a medical instrument having a hollow shaft on whose proximal end is positioned a handle consisting of at least two gripping members and on whose distal end there is a tool consisting of at least two jaw members, where at least one jaw member of the tool can be displaced with respect to the at least one other jaw member of the tool by means of a rotatably configured gripping member of the handle for opening and closing and the at least one displaceable jaw member and the corresponding gripping member of the handle serving to displace the jaw member are connected to one another by means of a push-pull rod that is mounted so that it can slide axially in the hollow shaft. In order also to reach operating areas located outside the instrument's longitudinal axis safely and with precision, it is proposed with the invention that the push-pull rod, which is mounted so that it can slide axially in the hollow shaft, can be moved by at least one spiral-shaped guide track into a rotary motion around its longitudinal axis.

13 Claims, 3 Drawing Sheets

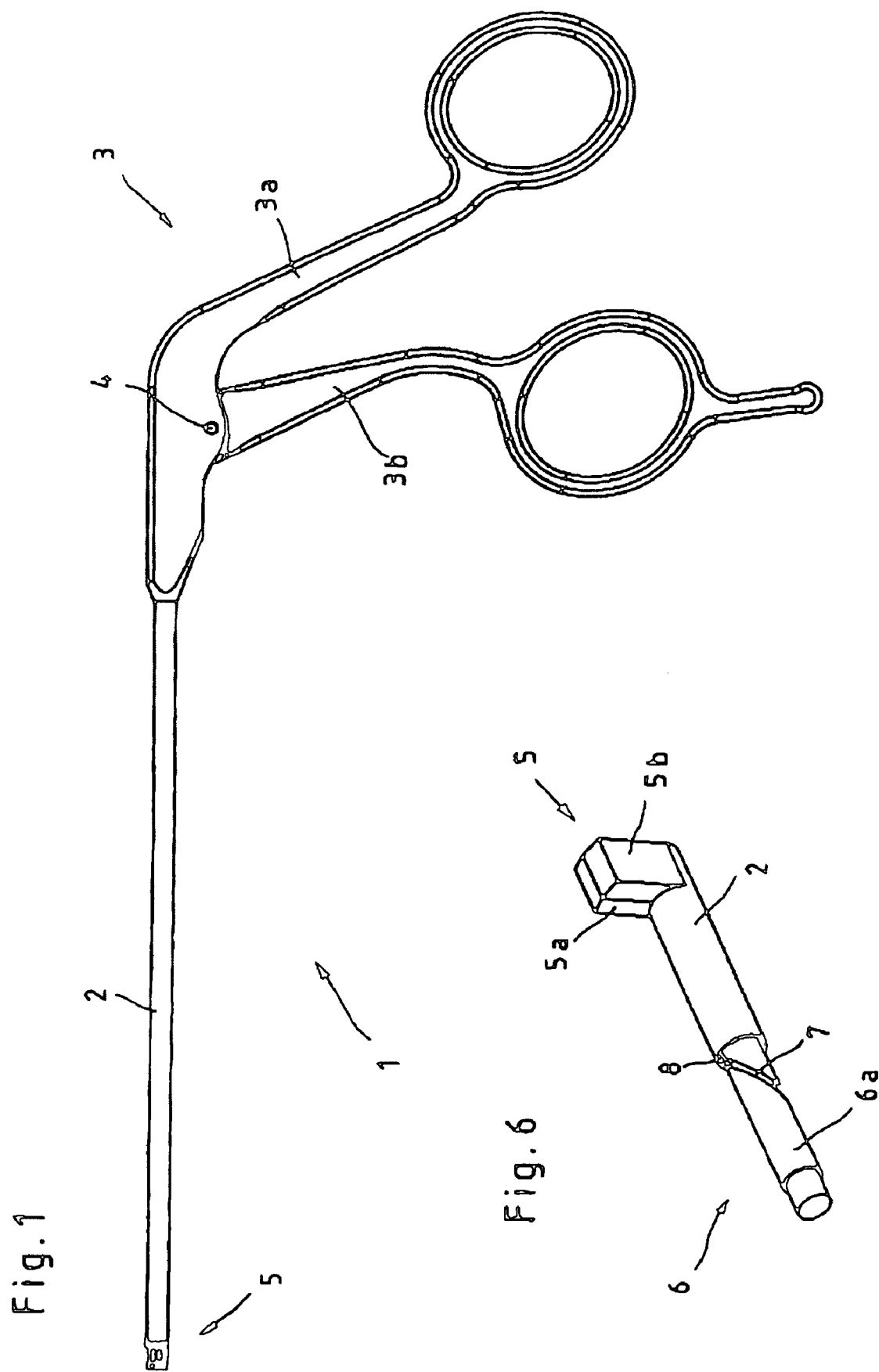

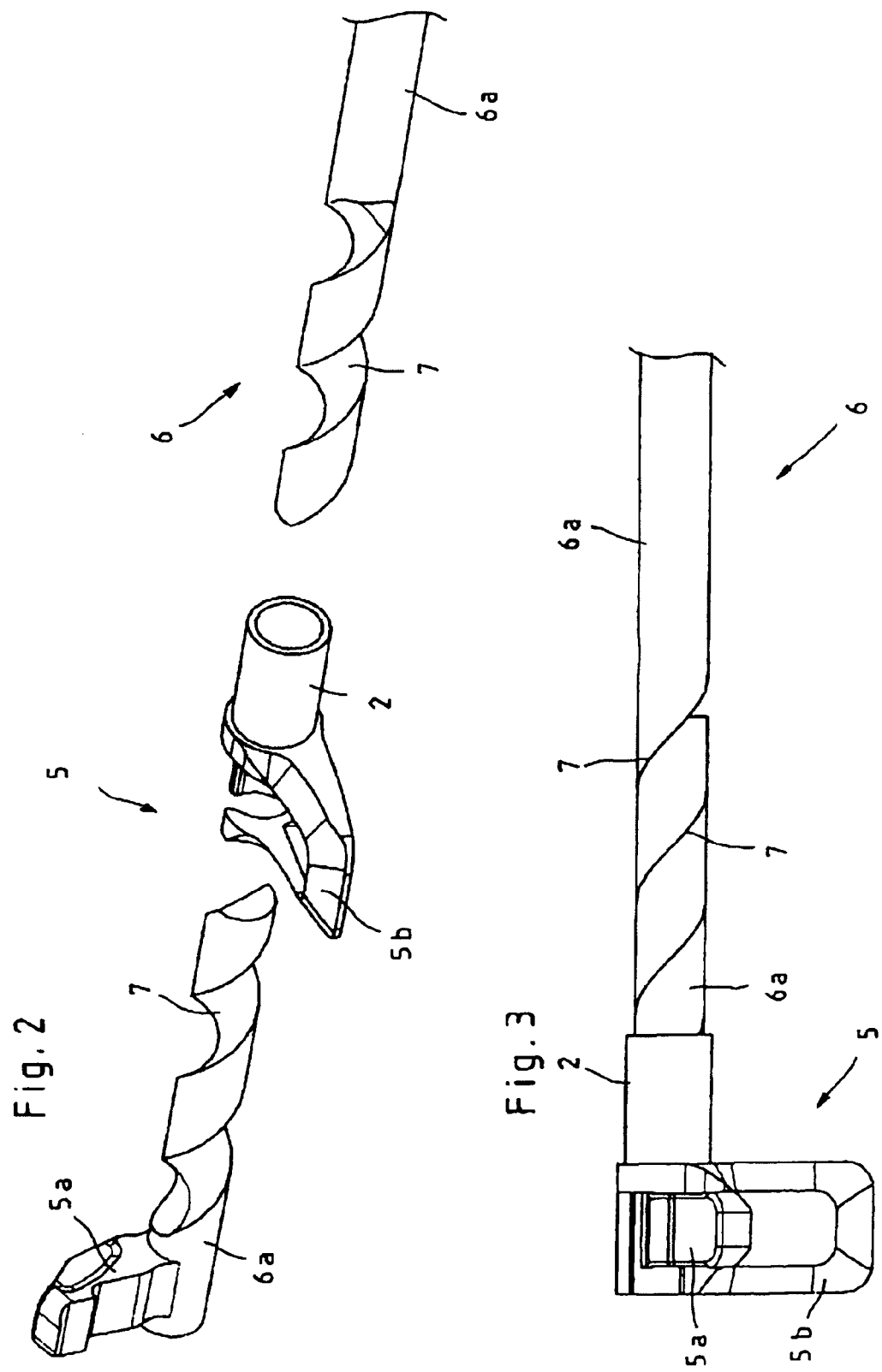

MEDICAL INSTRUMENT

FIELD OF THE INVENTION

The invention relates to a medical instrument having a hollow shaft on whose proximal end is positioned a handle consisting of at least two gripping members and on whose distal end there is a tool consisting of at least two jaw members, where at least one jaw member of the tool can be displaced with respect to the at least one other jaw member of the tool by means of a rotatably configured gripping member of the handle for opening and closing and the at least one displaceable jaw member and the corresponding gripping member of the handle serving to displace the jaw member are connected to one another by means of a push-pull rod that is mounted so that it can slide axially in the hollow shaft.

BACKGROUND OF THE INVENTION

Generic medical instruments in which the movable jaw member can be activated by means of a push-pull element, starting from a rotatable gripping member of the handle, have a variety of uses especially in endoscopic surgery, for instance as punches, scissors, needle holders, grasping instruments, and the like. In these instruments well known in the art, the jaw members that form the tool are as a rule positioned in the longitudinal direction of the instrument shaft, so that with these instruments it is possible to reach only operating areas that are positioned to be directly accessible, essentially in front of the tip of the instrument. However, because many operating areas are not accessible in a straight-line manner, these known instruments are either not at all appropriate for these purposes, or only to a limited extent.

Also known in the art are generic medical instruments in which the jaw members of the tool are turned laterally at an angle to the longitudinal axis of the shaft. Because in these instruments the rotatable jaw member of the tool makes a turning motion relative to the axial motion of the push-pull rod for opening and closing, it is necessary to convert the axial motion of the push-pull rod initiated by the motion of the handle into a rotary motion. For this purpose, based on experience in the art, it is customary to couple the handle and the push-pull rod together by means of a toothed gear. This configuration is relatively simple to produce; however, the transmission of power to the tool does not satisfy all operational requirements.

DE 103 27 655 A1 describes a generic medical instrument that has jaw members turned laterally at an angle to the longitudinal axis of the shaft and in which the motion is converted by means of a transmission lever that, on the one hand, is positioned on the push-pull rod and, on the other hand, is connected with the displaceable jaw member of the tool. This constructive conversion of axial motion into a rotary motion has thoroughly proven itself in the art, but it is expensive to produce.

Consequently it is the aim of the invention to produce a medical instrument of the aforementioned type, in which the conversion of axial motion of the push-pull rod into rotary motion of the displaceable jaw member can be achieved in simple and reliable fashion.

SUMMARY OF THE INVENTION

The solution of this aim according to the invention is characterized in that the push-pull rod that is mounted in the hollow shaft so that it can be slid axially can be moved through at least one spiral-shaped guide track into a rotary motion around its longitudinal axis.

Because of the configuration of the at least one spiral-shaped guide track, according to the invention, it is possible through constructively simple means to convert the axial motion of the push-pull rod into a rotary motion of the push-pull rod, an effect that is advantageous especially for medical instruments, whose jaw members are turned laterally at an angle to the longitudinal axis of the shaft.

In order to be able to transmit the rotary motion, which is transmitted into the push-pull rod, to the tool directly and as much as possible without an adverse effect on the power transmission, it is proposed with the invention that the displaceable jaw member is positioned at the distal end of the push-pull rod.

According to a first constructive embodiment of the invention, it is proposed that the spiral-shaped guide track is configured on the push-pull rod and the push-pull rod is advantageously configured in multiple parts, so that at least two portions of the push-pull rod can be connected to one another by means of spiral-shaped end portions. This embodiment of the invention, in which two portions of the push-pull rod are screwed together by means of spiral-shaped end portions, constitutes an especially compact and constructively simple way to transmit motion according to the invention.

With a practical embodiment of the invention, it is proposed that the push-pull rod is configured in two parts, so that the proximal portion can be secured on the rotatable gripping member of the handle and is configured on the distal end of the distal portion of the displaceable jaw member of the tool.

With the multipartite configuration of the push-pull rod, to prevent that the portion of the push-pull rod equipped with the displaceable jaw member can move in an axial direction in addition to the generated rotary motion, according to the invention the hollow shaft can be locked on the distal side.

It is further proposed with the invention that the portion of the push-pull rod connected with the handle is positioned on the rotatable gripping member of the handle in a manner so that it cannot rotate around its longitudinal axis, in order to transmit the rotary motion of the push-pull rod exclusively onto the portion of the push-pull rod equipped with the displaceable jaw member.

According to a second constructive embodiment of the invention, it is proposed that the spiral-shaped guide track is configured as a spiral-shaped groove in the surface of the push-pull rod, which interacts with a rigid abutment positioned on the inside of the hollow shaft.

This rigid abutment, which generates the rotary motion of the push-pull rod, can be configured, according to the invention, as a bolt engaging in the spiral-shaped groove or as a spiral-shaped counter-contour that corresponds with the spiral-shaped groove, so that the configuration of the spiral-shaped contours that engage with one another are characterized by low wear from friction.

According to a third constructive embodiment of the invention it is proposed that the spiral-shaped guide track is configured on the inside of the hollow shaft.

According to a practical embodiment of this constructive design, the spiral-shaped guide track is configured as a spiral-shaped groove on the inside of the hollow shaft, which interacts with a rigid abutment positioned on the surface of the push-pull rod, so that this rigid abutment is preferably configured as a bolt engaging in the spiral-shaped groove.

It is finally proposed with the invention that the push-pull rod is positioned so that it can rotate freely around its longitudinal axis on the rotatable gripping member of the handle, in order to enable the push-pull rod, which runs up against the rigid abutment, to rotate around its longitudinal axis if this axis is displaced in the axial direction by the rotatable gripping member.

Further characteristics and advantages of the invention can be seen from the description of the annexed illustrations, in which three embodiments of a medical instrument according to the invention are depicted in merely schematic form.

BRIEF DESCRIPTION OF THE DRAWINGS

FIG. 1 shows a side view of a medical instrument according to the invention.

FIG. 2 shows a detail perspective explosion view of the distal end of a medical instrument according to a first embodiment of the invention.

FIG. 3 shows a top view of the embodiment according to FIG. 2, but in assembled form.

FIG. 6 shows a perspective view according to FIG. 5, but depicting a third embodiment of the invention.

DETAILED DESCRIPTION OF THE INVENTION

Figure 4:
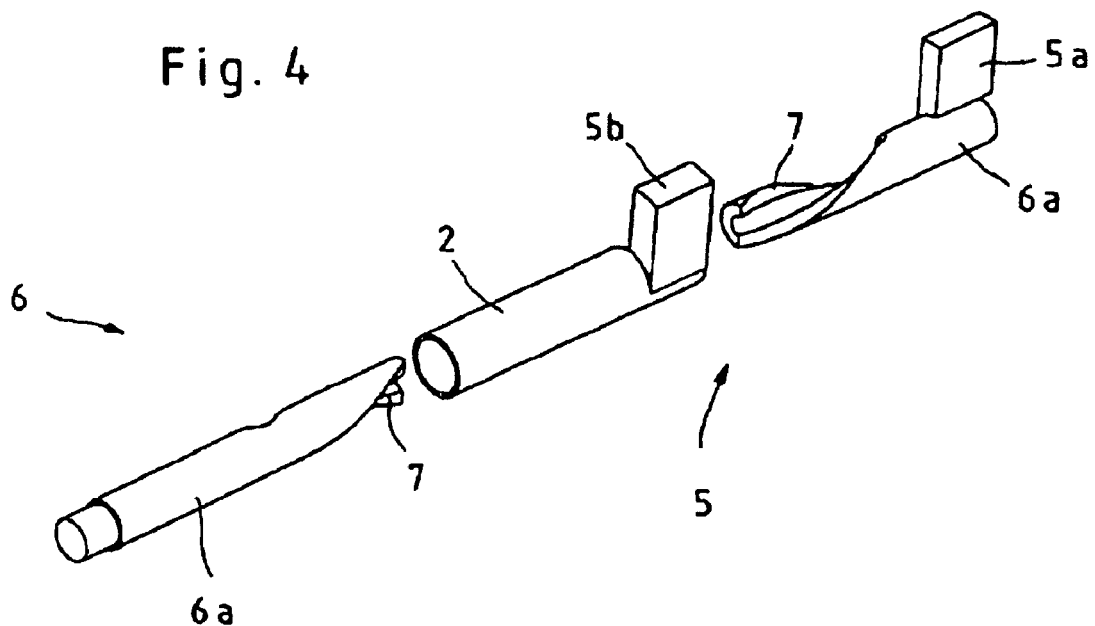
FIG. 4 shows a depiction according to FIG. 2, but showing a second embodiment of the invention.

The illustration in FIG. 1 shows a side view of a medical instrument 1, whose power transmission mechanism can have multiple uses, such as for instance for punches, scissors, needle holders, grasping instruments, and the like.

The medical instrument 1 consists essentially of a hollow shaft 2, on whose proximal end is positioned a handle 3 consisting of a rigid gripping portion 3a and a gripping portion 3b that can rotate with respect to the rigid gripping portion 3a around an axis of rotation 4. On the distal end of the shaft 2 there is a tool 5, which in the illustrated embodiment (FIGS. 2 and 3) consists of a rotatable jaw member 5a and a jaw member 5b connected rigidly with the shaft 2.

The illustrations in FIGS. 2 through 6 show that the jaw members 5a, 5b of the tool 5 are turned laterally at an angle to the longitudinal axis of the shaft 2. In the illustrated embodiments the jaw members 5a, 5b are each turned at a right angle to the longitudinal axis of the instrument shaft. Other angles between zero and 90 degrees, and even greater, are also possible, however.

Because of the angle of the tool 5 to the shaft 2, it is possible, using a medical instrument 1 configured in this way, to reach operating areas that are also difficult to access and which cannot be accessed on a direct straight-line path.

As can further be seen from FIGS. 2 through 6, the rotatable jaw member 5a is positioned on the distal end of a push-pull rod 6, which is positioned in the hollow shaft 2 and is connected with the rotatable gripping portion 3b of the handle 3 in such a way that from the rotation of the gripping portion 3b the rotatable jaw member 5a can be moved from a closed position to an open position or vice versa.

In order to be able to convert the sliding motion in axial direction, which is transmitted by activation of the rotatable gripping member 3b of the handle 3 to the push-pull rod 6, into a rotary motion for rotating the jaw member 5a of the tool 5, a spiral-shaped guide track 7 is configured on the push-pull rod 6.

In the embodiments illustrated in FIGS. 2 through 5, the push-pull rods 6 are each constructed of multiple parts, consisting of individual portions 6a. The ends of the portions 6a that face one another are configured in spiral form in such a way that in each case two spiral-shaped guide tracks 7 can be screwed together, as can be seen from FIGS. 3 and 5. The proximal portion 6a of the push-pull rod 6, as a supplement or alternative to the illustrated embodiment, can be extended and re-formed at will on the proximal side, depending on the handle 3 that is to be used each time.

In assembled condition, the distal end of the hollow shaft 2 is closed in order to prevent axial sliding of the portion 6a of the push-pull rod 6 that is equipped with the rotatable jaw member 5a. As soon as the push-pull rod 6 is pushed in axial direction in the hollow shaft 2 by means of the rotatable gripping portion 3b of the handle 3, this axial displacement of the proximal portion 6a of the push-pull rod 6 causes the spiral-shaped guide tracks 7 of the two portions 6a of the push-pull rod 6 to screw together or to unscrew from one another. Because the proximal portion 6a of the push-pull rod 6 is positioned, locked against turning, on the rotatable gripping portion 3b of the handle 3, the screwing or unscrewing of the spiral-shaped guide tracks 7 of the two portions 6a causes the distal portion 6a of the push-pull rod 6, equipped with the rotatable jaw member 5a, to carry out a rotary motion around its longitudinal axis, so that the rotatable jaw member 5a can be displaced between an open and a closed position.

Figure 5:
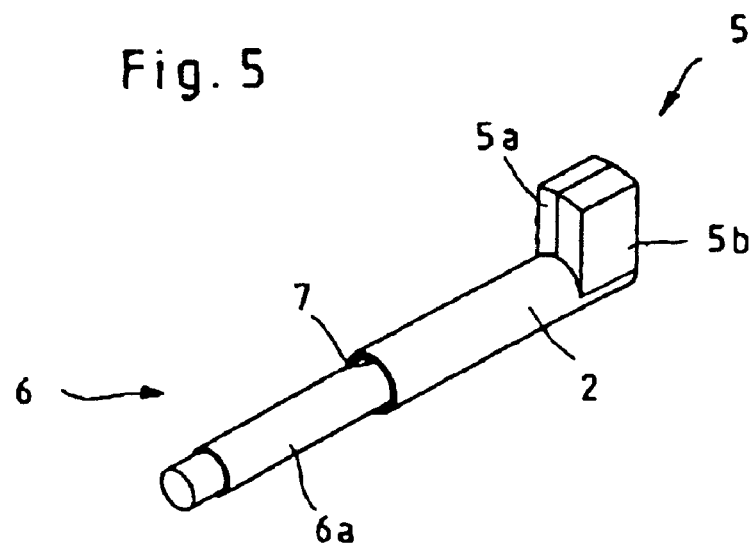
FIG. 5 shows a perspective view of the embodiment according to FIG. 4, but in assembled form.

The embodiments illustrated in FIGS. 2 and 4 are distinguished from one another in that the two spiral-shaped guide tracks 7 of the portions 6a of the push-pull rod 6 have one and one-half threads in the embodiment according to FIGS. 2 and 3, while in the embodiment according to FIGS. 4 and 5 the guide tracks 7 of each portion 6a have only one-half a thread.

Alternatively to the embodiments illustrated in FIGS. 2 through 5, for configuring or positioning the spiral-shaped guide tracks 7 it is also possible to configure the spiral-shaped guide tracks 7 as spiral-shaped groove in the surface of the push-pull rod 6, as illustrated in FIG. 6, or as a spiral-shaped groove on the inside of the hollow shaft 2, so that to produce the rotary motion on the inside of the hollow shaft 2 or on the surface of the push-pull rod 6, rigid abutments 8 are positioned, which interact with the corresponding spiral-shaped grooves.

In the embodiment illustrated in FIG. 6, the abutment 8 is configured as a bolt positioned on the inside of the hollow shaft 2 and engaging in the spiral-shaped groove.

In this type of design it is essential that the push-pull rod 6 is positioned so that it can freely rotate around its longitudinal axis on the rotatable gripping portion 3b of the handle 3, so that the push-pull rod 6, on running up against the corresponding abutment, can rotate around its longitudinal axis because of the activation of the rotatable gripping portion 3b.

A medical instrument of the aforementioned type is distinguished in that it is of simple construction and is simple to handle, while ensuring a uniform and safe conversion of the axial motion, which is transmitted by the rotatable gripping portion 3b to the push-pull rod 6, into a rotary motion of the rotatable jaw member 5a, with the greatest possible freedom of play in the power transmission.

What is claimed is:

1. A medical instrument having a hollow shaft, on whose proximal end is positioned a handle consisting of at least two gripping members and on whose distal end there is a tool consisting of at least two jaw members, so that at least one jaw member of the tool can be displaced for opening and closing with respect to the at least one other jaw member of the tool by means of a rotatably configured gripping member of the handle, and the at least one displaceable jaw member and the corresponding gripping member of the handle, serving to displace the jaw member, are connected to one another by a push-pull rod that is positioned so that it can slide axially in the hollow shaft, wherein the axially slidable push-pull rod positioned in the hollow shaft is set into a rotary motion around its longitudinal axis by at least one helical-shaped guide track characterized in that the push-pull rod is configured in several parts, wherein at least two portions of the push-pull rod are connected by helical-shaped end portions and the portion of the push-pull rod which is connected with the handle is positioned on the rotatable gripping member of the handle so that said portion of the push-pull rod cannot rotate around its longitudinal axis.

2. A medical instrument according to claim 1, characterized in that the displaceable jaw member is positioned on the distal end of the push-pull rod.

3. A medical instrument according to claim 1, characterized in that the helical-shaped guide track is configured on the push-pull rod.

4. A medical instrument according to claim 1, characterized in that the push-pull rod is configured in two parts, so that the proximal portion can be secured on the rotatable gripping member of the handle and is positioned on the distal end of the distal portion of the displaceable jaw member of the tool.

5. A medical instrument according to claim 1, characterized in that the hollow shaft can lock on the distal side.

6. A medical instrument according to claim 3, characterized in that the spiral-shaped guide track is configured as a spiral-shaped groove in the surface of the push-pull rod, which interacts with a rigid abutment positioned on the inside of the hollow shaft.

7. A medical instrument according to claim 6, characterized in that the rigid abutment positioned on the inside of the hollow shaft is configured as a bolt engaging in the spiral-shaped groove.

8. A medical instrument according to claim 6, characterized in that the rigid abutment positioned on the inside of the hollow shaft is configured as a spiral-shaped counter-contour corresponding with the spiral-shaped groove.

9. A medical instrument according to claim 1, characterized in that the spiral-shaped guide track is configured on the inside of the hollow shaft.

10. A medical instrument according to claim 9, characterized in that the spiral-shaped guide track is configured as a spiral-shaped groove on the inside of the hollow shaft, which interacts with a rigid abutment positioned on the surface of the push-pull rod.

11. A medical instrument according to claim 10, characterized in that the rigid abutment positioned on the surface of the push-pull rod is configured as a bolt engaging in the spiral-shaped groove.

12. A medical instrument according to claim 6, characterized in that the push-pull rod is positioned, freely rotatably around its longitudinal axis, on the rotatable gripping member of the handle.

13. A medical instrument according to claim 1, characterized in that the jaw members are turned laterally at an angle to the longitudinal axis of the shaft.

* * * * *